US009423239B2

(12) United States Patent
Gandhi

(10) Patent No.: US 9,423,239 B2
(45) Date of Patent: Aug. 23, 2016

(54) METHOD TO IMPROVE FIBER LENGTH MEASUREMENT USING CONFOCAL LASER SCANNING MICROSCOPE IMAGES

(71) Applicant: Toyota Motor Engineering & Manufacturing North America, Inc., Erlanger, KY (US)

(72) Inventor: Umesh N. Gandhi, Farmington Hills, MI (US)

(73) Assignee: Toyota Motor Engineering & Manufacturing North America, Inc., Erlanger, KY (US)

(*) Notice: Subject to any disclaimer, the term of this patent is extended or adjusted under 35 U.S.C. 154(b) by 0 days.

(21) Appl. No.: 14/577,941

(22) Filed: Dec. 19, 2014

(65) Prior Publication Data

US 2016/0178349 A1  Jun. 23, 2016

(51) Int. Cl.
| | |
|---|---|
| *G01B 11/02* | (2006.01) |
| *G02B 21/00* | (2006.01) |
| *G01M 11/00* | (2006.01) |
| *G01N 33/34* | (2006.01) |
| *G01N 33/36* | (2006.01) |

(52) U.S. Cl.
CPC ............... *G01B 11/02* (2013.01); *G01M 11/30* (2013.01); *G02B 21/0024* (2013.01); *G01N 33/34* (2013.01); *G01N 33/36* (2013.01)

(58) Field of Classification Search
None
See application file for complete search history.

(56) References Cited

U.S. PATENT DOCUMENTS

| 5,638,206 | A | 6/1997 | Sumiya et al. |
| 5,804,813 | A | 9/1998 | Wang et al. |
| 6,806,955 | B2 | 10/2004 | Jang |
| 2009/0279743 | A1* | 11/2009 | Li ............ G01N 15/1463 382/111 |
| 2010/0104846 | A1* | 4/2010 | Sano ............ D01F 9/145 428/297.4 |

OTHER PUBLICATIONS

Otsu, N., "A threshold selection method from gray-level histrograms", IEEE Transactions on Systems, Man and Cybernetics SMC-9:62-6 (1979).*
Saggese et al; "Development of a method for the measurement of primary cilia length in 3D"; Cilia, 1:11; 2012, in 12 pages.
Wu et al; "Automated quantification and reconstruction of collagen matrix from 3D confocal datasets"; Journal of Microscopy; May 2003; pp. 158-165; vol. 210, Pt. 2.
Janacek et al.; "3D Visualization and Measurement of Capillaries Supplying Metabolically Different Fiber Types in the Rat Extensor Digitorum Longus Muscle During Denervation and Reinnervation"; Journal of Histochemistry & Cytochemistry <http://www.jhc.org>; 2009; pp. 437-447; vol. 57(5).

* cited by examiner

*Primary Examiner* — Kara E Geisel
*Assistant Examiner* — Shawn Decenzo
(74) *Attorney, Agent, or Firm* — Christopher G. Darrow; Darrow Mustafa PC

(57) ABSTRACT

A method for measuring the lengths of industrial fibers is provided. The method employs the depth perception properties of a confocal laser microscope to monitor three-dimensional properties of the sample to determine fiber connectivity in areas where individual fibers in the sample overlap one another. This results in a more accurate matching of fiber termini in such situations, and obviates the need for algorithms which match fiber termini based on curvature, angle, or other two-dimensional properties.

9 Claims, 4 Drawing Sheets

METHOD TO IMPROVE FIBER LENGTH MEASUREMENT USING CONFOCAL LASER SCANNING MICROSCOPE IMAGES

TECHNICAL FIELD

The present invention relates in general to a method for measuring the lengths of industrial fibers in a sample.

BACKGROUND

It is very important to measure the length of fiber in polymers. Typically when analyzing a sample of fibers many of the individual fibers will overlap one another, making it difficult to determine which fiber termini belong to the same fiber and therefore difficult to confidently measure the lengths of individual fibers.

Confocal laser microscopes have the ability to analyze a microscopy sample in two-dimensions, but also to analyze a third dimension of depth, or distance between the sample and the microscope. In particular, a confocal laser microscope will give a differing signal intensity based on sample depth.

SUMMARY

A method for measuring fiber length in an industrial fiber sample is provided. The method includes a first step of providing an industrial fiber sample, the industrial fiber sample having at least two overlapping fibers, the at least two overlapping fibers defining an overlap region. The method includes a second step of measuring signal intensity within the overlap region using a confocal laser microscope. The method includes a step of distinguishing contiguous areas of signal intensity continuity from contiguous areas of signal intensity discontinuity and a step of identifying an individual fiber on the basis of these distinctions. The method finally includes a step of measuring the length of the identified individual fiber.

A system for automated measurement of fiber length is also disclosed. The system includes a confocal laser microscope positioned to direct confocal illumination at a sample analysis surface, and a controller configured to direct the confocal laser microscope to perform a two-dimensional sample scan, to detect an overlap region from the two-dimensional image data, and to direct the confocal laser microscope to perform a confocal intensity scan of the overlap region. The controller can employ an algorithm to automatically measure a fiber length based on the two-dimensional and confocal intensity data obtained.

BRIEF DESCRIPTION OF THE DRAWINGS

Various aspects and advantages of the invention will become apparent and more readily appreciated from the following description of the embodiments taken in conjunction with the accompanying drawings, of which.

DETAILED DESCRIPTION

Disclosed herein is a method for measuring the lengths of industrial fibers that are grouped in a sample in which different fibers are overlapping. The method is expected to be highly accurate and does not require elaborate algorithms used by other methods.

The disclosed method employs confocal laser microscopy to analyze fiber overlaps and thereby determine which pairs of fiber termini in an overlapping cluster belong together.

The term "fiber" as used herein refers to a flexible material of homogenous composition and thread-like shape. A fiber of the present disclosure will typically have a maximum dimension at or below the visibility limit to the human eye, for example a fiber length may range from about 100 μm to 2 mm. A fiber of the present disclosure will typically have a width or diameter in the range of one to fifty μm. In some instances, a fiber can have an aspect ratio in the range of 100 to 500.

The phrase "industrial fiber" as used herein generally refers to a synthetic or semi-synthetic fiber although natural fibers may also be used. Non-limiting examples of industrial fibers include cellulose, silicon carbide, organic polymer fiber, carbon fiber, and fiberglass. Industrial fibers are often used in meshed materials, woven materials, or as reinforcing elements of composite materials. In the last case, industrial fibers may be entrained in a polymeric matrix to enhance strength or alter other properties. In many industrial fiber deployments, it is desirable to know the lengths of industrial fibers in a sample, and length determination is often made by direct measurement with the assistance of magnification. Difficulty arises however when fibers in a sample are overlapped.

Figure 1A:
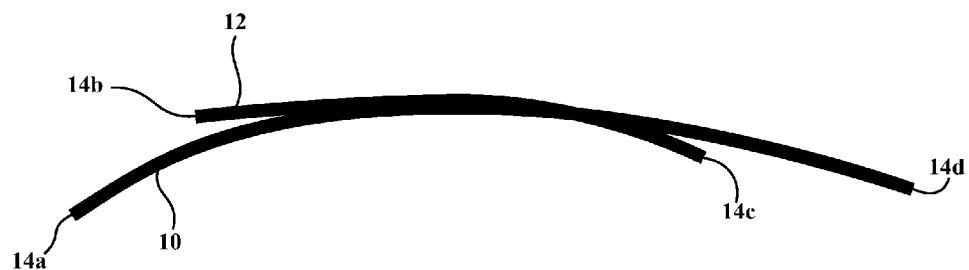
FIG. 1A is a plan view of a schematic illustration of two industrial fibers having an overlap region and substantial longitudinal alignment.

Referring now to FIG. 1A, first and second fibers 10, 12 are shown at approximately 100× magnification. The first and second fibers 10, 12 have fiber ends 14a, 14b, 14c, and 14d. While the first and second fibers 10, 12 overlap one another, it may be difficult to tell by standard microscopy which of the first and second fibers 10, 12 passes over the other in the direction of view. In addition, because the first and second fibers 10, 12 have significant longitudinal alignment, it is difficult to correctly pair fiber ends 14a, 14b, 14c, and 14d and therefore difficult to measure the length of either of the first and second fibers 10, 12. For example, the first fiber 10 could include paired fiber ends 14a and 14c or it could include paired fiber ends 14a and 14d. An incorrect determination or guess of the paired fiber ends on fiber 10 would lead to an incorrect length measurement.

Figure 1B:
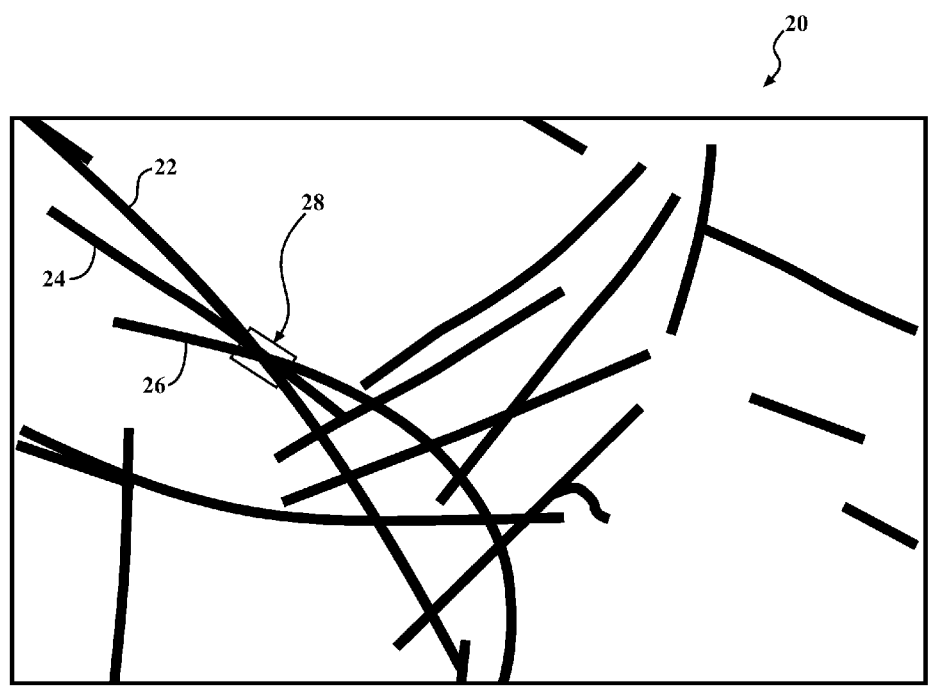
FIG. 1B is an exemplary overhead microscopic view of an industrial fiber sample prepared for length measurement.

FIG. 1B shows a recreation of a microscopic photograph of a fiber sample 20, the image of FIG. 1B having about 50× magnification. It is to be understood that, in many instances, fiber sample 20 will be a sample of industrial fibers. Fiber sample 20 includes a first fiber 22, a second fiber 24, and a third fiber 26, each of the first, second, and third fibers 22, 24, 26 passing through an overlap region 28.

A fiber sample 20 such as that shown in FIG. 1B can be obtained prior to deployment of the fibers in a material, or can include fibers recovered from a deployed material. For example, industrial fibers deployed in a composite material can frequently be recovered by removing the polymeric matrix, for example by burning, melting, or dissolving the polymeric matrix, depending on the combustion temperatures, melting temperatures, or solubilities of the fibers and polymeric matrix.

Figure 2A:
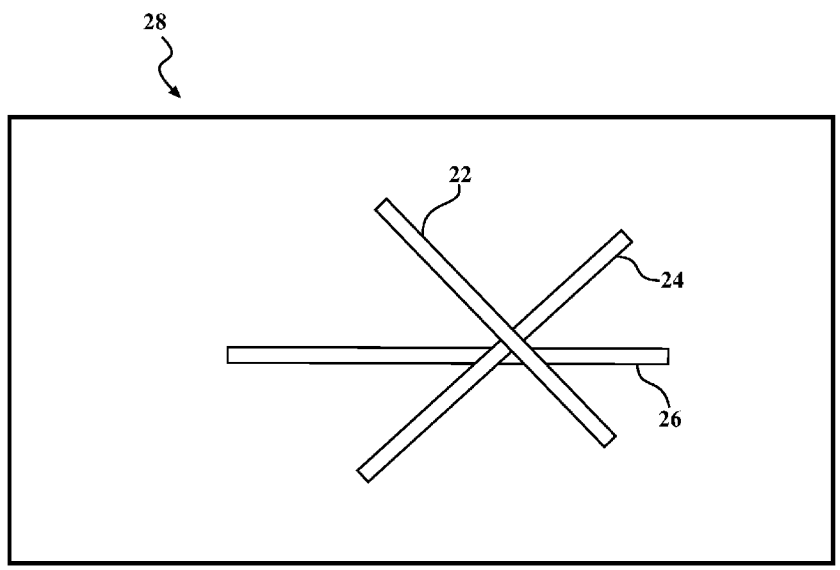
FIG. 2A is a schematic overhead view of three industrial fibers to be measured using the method of FIG. 3.
Figure 2B:
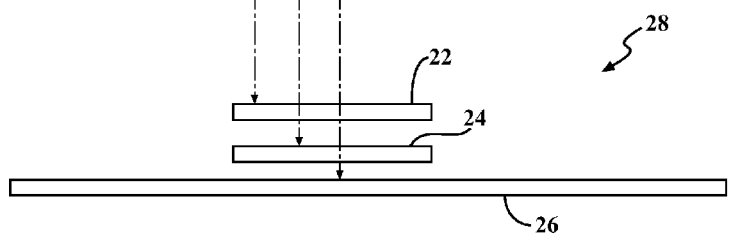
FIG. 2B is a side view of the three industrial fibers of FIG. 2A positioned within the field of view of a confocal laser microscope.

FIG. 2A shows an overhead view of an overlap region 28 of an industrial fiber sample having fibers 22, 24, 26. FIG. 2B shows a side view of the overlap region 28 with a confocal laser microscope 50 positioned above. As should be understood, the overlap region 28 can vary in size and shape based on the particular fibers and their spatial arrangement. Due to the ability of the confocal laser microscope 50 to measure signal intensity based on distance between the microscope and sample region, or sample depth, the confocal laser microscope 50 is able to provide data suitable to determine fiber connectivity for each of the three fibers 22, 24, 26. Thus, it is possible to determine, in the example of FIG. 2B, that fiber 22 overlaps fiber 24 and that fiber 24 overlaps fiber 26, based on signal intensity. This then allows for matching of fiber termini by monitoring fiber connectivity across the length of each fiber 22, 24, 26.

While the confocal laser microscope 50 utilized in the method 100 can utilize fluorescence confocal microscopy to analyze the fiber sample 20, for example by attaching fluorophores to individual fibers, it is anticipated that reflection confocal microscopy will be frequently utilized. The confocal laser microscope 50 can in some implementations be utilized for two-dimensional scanning of the fiber sample 20 as well as depth determination within the at least one overlap region 28.

Figure 3:
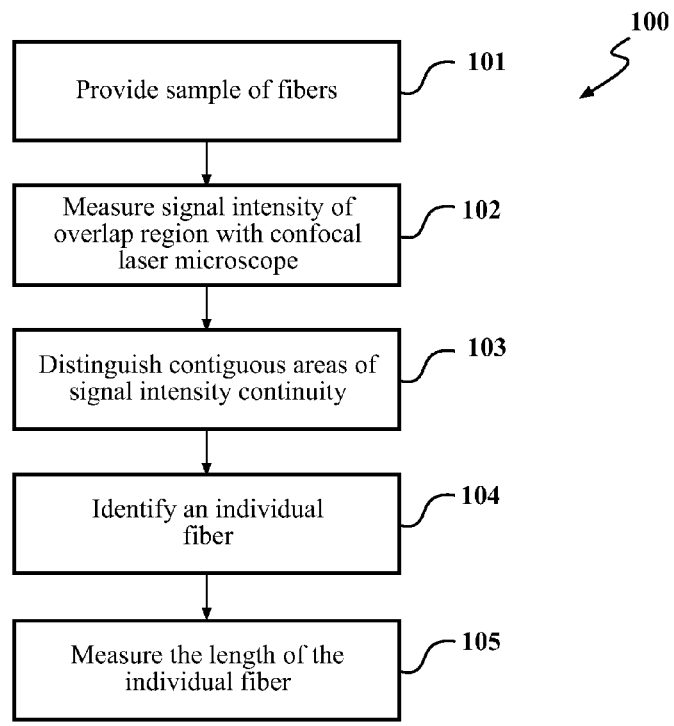
FIG. 3 is a flow diagram of a method for measuring lengths of industrial fibers contained in a sample of the type shown in FIG. 1B.

Referring now to FIG. 3, a method 100 for measuring the lengths of individual fibers includes a first step 101 of providing a fiber sample, such as a fiber sample 20. The fiber sample 20 will typically have at least two fibers, such as first, second, and third fibers 22, 24, 26 that define an overlap region 28.

In a second step 102 of method 100, and with continued reference to FIGS. 2A and 2B, signal intensity is measured in an area adjacent to and/or within the overlap region 28 using a confocal laser microscope 50. The confocal laser microscope can focus illumination light at a point in a focal plane such that intensity of detected light (e.g. reflected or fluoresced light) will be proportional to the proximity of the reflecting or fluorescing sample surface to the focal plane. Thus, the confocal laser microscope 50 can be focused at a focal plane parallel to and located some distance, such as an average cross sectional diameter of fibers, above a surface on which the industrial fiber sample is supported. Any fiber surfaces located above or below the focal plane (i.e. nearer or farther, respectively to the confocal lens than is the focal plane) will produce a weaker detectable signal than those surfaces located at the focal plane. For example, and with specific reference to FIG. 2A, overlapping fiber 22 can have a signal intensity at points distant from fibers 24 and 26 if the focal plane is a fiber diameter above the supporting surface, but the signal intensity will be lower at points on fiber 22 where fiber 22 is resting on top of fibers 24 and 26 such that fiber 22 is above the focal plane at those points. Fiber 26 can have a consistently high signal intensity across its entire length, except where it is covered by fiber 22 and/or fiber 24.

In a third step 103 of method 100, contiguous areas of signal continuity and contiguous areas of signal discontinuity are distinguished within the overlap region 28. In general terms, "contiguous areas of signal continuity" refers to a portion of the overlap region in which signal intensity is uniform or changes only gradually, whereas "contiguous areas of signal discontinuity" refers to a portion of the overlap region within which there is a relatively abrupt difference in signal intensity. In more specific terms, "contiguous areas of signal continuity" can comprise two points within an overlap region 28, the two points spatially separated by no more than a specific distance (a "contiguity distance") and having a signal intensity difference not greater than a defined amount (an "intensity continuity threshold"). Distinction between contiguous areas of signal continuity and contiguous areas of signal discontinuity can be made by a user through visual examination, or by a controller apparatus operating an algorithm.

In implementations wherein the distinguishing step 103 is performed by a controller apparatus operating an algorithm, the method 100 can include additional steps of designating an absolute intensity threshold, defining an intensity continuity threshold, and setting a contiguity distance. The absolute intensity threshold is a minimum signal intensity to be applied at the measuring step 102, such that a portion of the overlap region 28 having signal intensity less than the absolute intensity threshold can be ignored in the distinguishing step 103. As mentioned above, the intensity continuity threshold is also an intensity value that can be employed in the distinguishing step 103. Contiguous areas having a signal intensity difference less than the intensity continuity threshold can be distinguished as contiguous areas of intensity continuity, while contiguous areas having an intensity difference greater than the intensity continuity threshold can be distinguished as contiguous areas of intensity discontinuity. Also, as mentioned above, the contiguity distance is a value having units of distance and can be used to define whether areas are contiguous. Two points separated by a distance less than the contiguity distance can be deemed contiguous areas, while two points separated by a distance greater than the contiguity distance can be deemed not contiguous.

The method 100 can include an additional step 104 of identifying an individual fiber within the overlap region, on the basis of the distinction between contiguous areas of intensity continuity or discontinuity. In one implementation, an individual fiber can be identified as a fiber occupying only contiguous areas of signal intensity continuity. In another implementation, an individual fiber can be identified as a fiber occupying contiguous areas of signal intensity continuity interrupted by a contiguous area of signal intensity discontinuity.

Referring again to FIG. 2A, first fiber 22 can be identified as an individual fiber based on its occupancy only of contiguous areas of signal intensity continuity. Second fiber 24 can be identified as an individual fiber based on the fact that the signal intensities of its portions on either side of the crossing junction are continuous with one another, but are interrupted by the short signal intensity discontinuity of overlapping first fiber 22.

In another step 105 of the method 100, the length of the identified individual fiber is measured. In general terms, an individual fiber can be identified in step 104 by the individual fibers occupancy of contiguous areas of signal intensity continuity. For example, an individual fiber which lies across the top (i.e. nearest the confocal laser microscope 50) of an overlap region 28, such as overlapping first fiber 22 of FIG. 2A, the individual fiber can be identified by occupancy only of contiguous areas of signal intensity continuity. In such an instance, the maximum linear or curvilinear length of contiguous areas of signal intensity continuity can represent the length of the individual fiber.

Figure 4:
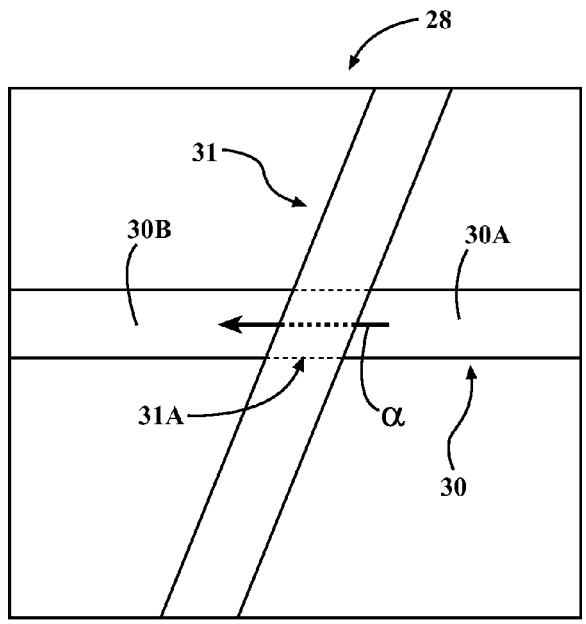
FIG. 4 is a schematic overhead view of an upper fiber crossing a lower fiber, the upper fiber presenting an interruption in confocal microscope signal intensity continuity along a longitudinal direction of the lower fiber.

In some instances, an individual fiber can be identified in step 104 by the individual fibers occupancy of interpolated contiguous areas of signal intensity continuity. FIG. 4 illustrates an example in which identification of an individual fiber based on occupancy of interpolated contiguous areas of signal intensity continuity can be accomplished. FIG. 4 shows an overlap region 28 wherein a lower (i.e. farther from the confocal laser microscope 50) fiber 30 is overlapped with an upper (i.e. nearer to the confocal laser microscope 50) fiber 31. Lower fiber 30 occupies a first region 30A of contiguous areas of signal intensity continuity and a second region 30B of contiguous areas of signal intensity continuity, but the complete contiguous areas of signal intensity continuity of lower fiber 30 are interrupted by upper fiber 31, and in particular by contiguous areas of signal intensity discontinuity bounding the interrupting region 31A. In such a scenario, lower fiber 31 can be identified as an individual fiber in step 104 through a process of extrapolation and/or interpolation. For example, beginning at the point at which the first region 30A contacts the interrupting region 31A, signal intensity continuity can be extrapolated in the direction of the arrow a. If the region of extrapolated signal intensity values encounter a matching region of detected contiguous areas of signal intensity continuity, such as in the second region 30B, then the individual fiber 30 can be identified as including the first region 30A and the second region 30B. As will be obvious to one skilled in the art, such an extrapolation and/or interpolation analysis can be performed in either direction, or bi-directionally. In some variations, matching of extrapolated and/or interpolated signal intensity continuity with a region having detected contiguous areas of signal intensity continuity can include an error margin. Such an error margin can be termed an "interpolation margin". In some variations, extrapolation and/or interpolation of signal intensity continuity can be limited to a maximum distance. Such a maximum distance can be termed an "interpolation distance". In some variations, determination of interpolated contiguous areas of signal intensity continuity may be performed only if interrupting region (e.g. 31A) has signal intensity greater than the absolute intensity threshold.

Also disclosed is a system for automated measurement of fiber length. The system can include a sample analysis surface and a confocal laser microscope 50 positioned to focus an illumination beam at a focal plane positioned at or adjacent to the sample analysis surface. The system can optionally include a controller configured to automate two-dimensional scanning of a fiber sample 20 placed on the sample analysis surface. In some implementations, the controller can be configured to identify an overlap region 28. In such implementations, the controller can then perform steps 102, 103, 104, and 105 of the method 100 as described above to measure the length of a fiber in the overlap region 28. The controller can make use of an algorithm which employs an absolute intensity threshold, an intensity continuity threshold, and/or a contiguity distance, as disclosed above.

Figure 5:
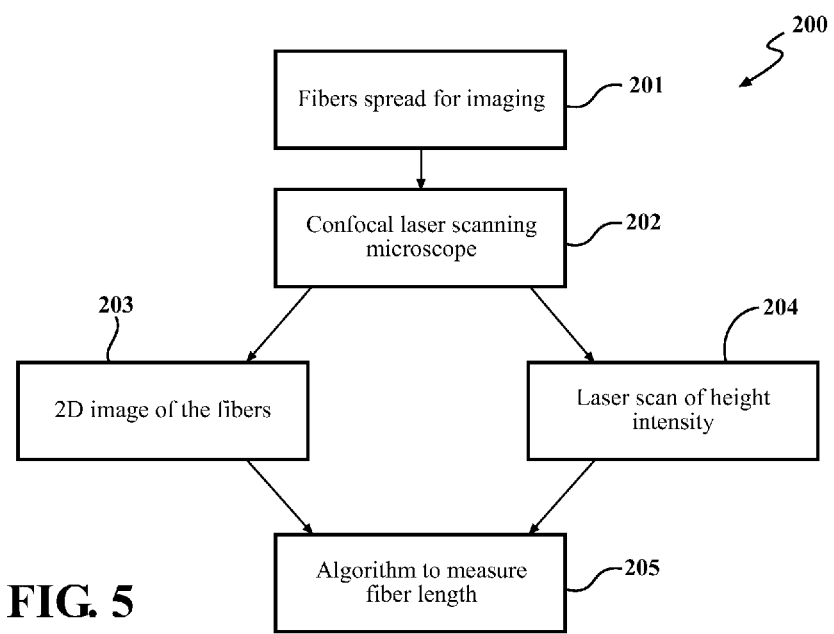
FIG. 5 is a flow diagram of a method of the type shown in FIG. 3 with additional steps.

FIG. 5 provides additional steps such as in a method 200 for measuring industrial fiber length. The method 200 is based on the method 100, but may be useful for adaptation to an automated system for measuring fiber length. In a first step 201, a sample of industrial fibers 20 is spread on a sample analysis surface, either by a user or by an automated/robotic assembly. In steps 202/203, a controller directs a confocal laser microscope 50 to perform a two-dimensional scan of the fiber sample 20, the controller subsystem detecting an overlap region 28 from the two-dimensional image data. In steps 202/204, the controller directs the confocal laser microscope to perform a confocal intensity scan of the overlap region 28. In step 205, the controller uses an algorithm to distinguish contiguous areas of signal intensity continuity from contiguous areas of signal intensity discontinuity; to identify and individual fiber within the overlap region; and to measure the length of the identified individual fiber; as disclosed above.

The foregoing description relates to what are presently considered to be the most practical embodiments. It should be understood that in the discussion of various methods having a number of steps, the disclosed steps can be performed independently or can be combined. In addition, the discussion of steps in a particular order is not intended to imply limitation to any chronological order. It is to be understood that the disclosure is not to be limited to specific examples discussed but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for measuring fiber length comprising:
providing a fiber sample, the fiber sample having at least two overlapping fibers, the at least two overlapping fibers defining an overlap region;
measuring signal intensity within the overlap region using a confocal laser microscope;
defining an absolute intensity threshold as a minimum signal intensity to be applied at the measuring signal intensity step, such that any portion of the overlap region having signal intensity less than the absolute intensity threshold is excluded from a subsequent step;
distinguishing contiguous areas of signal intensity continuity from contiguous areas of signal intensity discontinuity by a process that includes:
defining a contiguity distance, having units of distance; and
defining a signal intensity continuity threshold, having units of signal intensity,
wherein an area of signal intensity continuity comprises two continuity points, both continuity points having a signal intensity above the absolute intensity threshold, the two continuity points separated by the contiguity distance and having a signal intensity difference not greater than the signal intensity continuity threshold; and
wherein an area of signal intensity discontinuity comprises two discontinuity points, both discontinuity points having a signal intensity above the absolute intensity threshold, the two discontinuity points separated by the contiguity distance and having a signal intensity equal to or greater than the signal intensity continuity threshold;
identifying an individual fiber of the at least two overlapping fibers within the overlap region, the individual fiber comprising areas of signal intensity continuity; and
measuring the length of the identified individual fiber.

2. The method as recited in claim 1, comprising:
identifying at least one interrupting region where a contiguous area of signal intensity discontinuity borders a contiguous area of signal intensity continuity;
extrapolating signal intensity for a distance along a vector from the contiguous area of signal intensity continuity across the interrupting region;
defining an interpolated contiguous area of signal intensity continuity where the extrapolated signal intensity matches, within an error margin, a measured signal intensity within the distance;
wherein the individual fiber comprises the interpolated contiguous area of signal intensity continuity.

3. The method as recited in claim 1, wherein providing the fiber sample comprises providing a sample of industrial fibers.

4. The method as recited in claim 3, wherein the providing the fiber sample comprises providing a sample of synthetic fibers.

5. The method as recited in claim 4, wherein providing the fiber sample comprises providing a sample of industrial fibers selected from the group consisting of carbon fiber and fiberglass.

6. The method as recited in claim 1, wherein the confocal laser microscope utilizes reflection confocal microscopy.

7. A system for automated fiber length measurement, the system comprising:
- a confocal laser microscope; and
- a controller configured to direct the confocal laser microscope to perform a two-dimensional scan of a sample of fibers, to identify an overlap region comprising portions of at least two overlapping fibers, and to direct the confocal laser microscope to perform a confocal intensity scan of the overlap region;
- wherein the system employs an algorithm to measure a length of a fiber present in the overlap region, the algorithm comprising:
  - defining an absolute intensity threshold as a minimum signal intensity, such that any portion of the overlap region having signal intensity less than the absolute intensity threshold is excluded from a subsequent step;
  - distinguishing contiguous areas of signal intensity continuity from contiguous areas of signal intensity discontinuity by a process that includes:
    - defining a contiguity distance; and
    - defining a signal intensity continuity threshold,
      - wherein an area of signal intensity continuity comprises two continuity points, both continuity points having a signal intensity above the absolute intensity threshold, the two continuity points separated by the contiguity distance and having a signal intensity difference not greater than the signal intensity continuity threshold; and
    - wherein an area of signal intensity discontinuity comprises two discontinuity points, both discontinuity points having a signal intensity above the absolute intensity threshold, the two discontinuity points separated by the contiguity distance and having a signal intensity equal to or greater than the signal intensity continuity threshold;
  - identifying an individual fiber of the at least two overlapping fibers within the overlap region, the individual fiber comprising areas of signal intensity continuity; and
  - measuring the length of the identified individual fiber.

8. The system as recited in claim 7, wherein the confocal laser microscope utilizes reflection confocal microscopy.

9. The system as recited in claim 7, wherein the algorithm comprises:
- identifying at least one interrupting region where a contiguous area of signal intensity discontinuity borders a contiguous area of signal intensity continuity;
- extrapolating signal intensity for a distance along a vector from the contiguous area of signal intensity continuity across the interrupting region;
- defining an interpolated contiguous area of signal intensity continuity where the extrapolated signal intensity matches, within an error margin, a measured signal intensity within the distance;
- wherein the individual fiber comprises the interpolated contiguous area of signal intensity continuity.

* * * * *